(12) United States Patent
Bennet

(10) Patent No.: US 12,357,669 B1
(45) Date of Patent: Jul. 15, 2025

(54) MODIFICATION OF NATURAL COMPOUNDS TO CREATE PRODUCTS WITH ENHANCED HEALTH BENEFITS

(71) Applicant: Justin David Bennet, Aptos, CA (US)

(72) Inventor: Justin David Bennet, Aptos, CA (US)

( * ) Notice: Subject to any disclaimer, the term of this patent is extended or adjusted under 35 U.S.C. 154(b) by 0 days.

(21) Appl. No.: 18/826,102

(22) Filed: Sep. 5, 2024

(51) Int. Cl.
| | | |
|---|---|---|
| *A61K 36/82* | (2006.01) | |
| *A61K 31/355* | (2006.01) | |
| *A61K 36/81* | (2006.01) | |
| *A61K 47/52* | (2017.01) | |
| *A61P 1/04* | (2006.01) | |
| *A61P 29/00* | (2006.01) | |

(52) U.S. Cl.
CPC ............ *A61K 36/82* (2013.01); *A61K 31/355* (2013.01); *A61K 36/81* (2013.01); *A61K 47/52* (2017.08); *A61P 1/04* (2018.01); *A61P 29/00* (2018.01); *A61K 2236/331* (2013.01); *A61K 2236/51* (2013.01); *A61K 2236/53* (2013.01)

(58) Field of Classification Search
None
See application file for complete search history.

(56) References Cited

U.S. PATENT DOCUMENTS 4,617,317 A * 10/1986 Bennet .................. A61P 35/00
514/458
2006/0115468 A1* 6/2006 Morrison ........... A61K 38/4873
424/769

* cited by examiner

*Primary Examiner* — Terry A McKelvey
*Assistant Examiner* — Catheryne Chen
(74) *Attorney, Agent, or Firm* — PatentPC; Bao Tran

(57) ABSTRACT

A method for treating a gastrointestinal condition includes preparing an aqueous extract of bioactive compound by adding dried green tea material to hot water and filtering the aqueous extract; adding a solution of an iron-containing compound to the filtered aqueous extract to form a complex or chelate of the bioactive compounds with iron; and drying the solution at a temperature between 80 to 150 degrees Fahrenheit to obtain a fine granular or powdered state.

13 Claims, 2 Drawing Sheets

MODIFICATION OF NATURAL COMPOUNDS TO CREATE PRODUCTS WITH ENHANCED HEALTH BENEFITS

BACKGROUND OF THE INVENTION

Gastrointestinal health is a crucial aspect of overall well-being, affecting not only digestion but also the immune system, nutrient absorption, and mental health. The gastrointestinal tract can be subjected to a variety of disorders, ranging from minor discomforts such as bloating and heartburn to more severe conditions such as inflammatory bowel disease, peptic ulcers, and colorectal cancer. Conventional treatments for gastrointestinal issues typically include pharmaceuticals that can cause adverse side effects and may not be suitable for long-term use.

SUMMARY OF THE INVENTION

In one aspect, a method is disclosed for forming a compound useful in promoting gastrointestinal health and addressing gastrointestinal and extraintestinal conditions. This method includes the preparation of an aqueous extract rich in bioactive compounds, achieved by infusing dried green tea material in hot water, followed by filtration to purify the extract. Post-filtration, an iron-containing compound solution is introduced to the extract, initiating the formation of a complex or chelate and/or complex between the bioactive compounds and iron. The resultant solution is then dried, yielding a product in a fine granular or powdered form, suitable for consumption or further processing.

In another aspect, a method for enhancing gastrointestinal health and treating both gastrointestinal and extraintestinal conditions is disclosed. The process includes steeping dried plant material in hot water ranging from 100 to 200 degrees Fahrenheit under mild agitation for approximately 3 minutes, followed by a filtration step. Next, an iron-containing compound, which can be ferrous sulfate, ferrous gluconate, ferric chloride, or ferrous fumarate, is added to the filtered extract. This addition creates a complex or chelate between the bioactive compounds and iron. The final step involves drying the resultant solution to produce a fine granular or powdered product. This therapeutic approach leverages the beneficial properties of green tea extract chelated/complexed with iron to ameliorate the symptoms of ulcerative colitis. This is an effect not seen with green tea extract alone, iron alone or the two administered together without the prior formation of the chelate/complex. This is achieved by preparing an aqueous extract of chelated/complexed bioactive compounds from green tea.

In a further aspect, a method treats ulcerative colitis in a patient by administering a composition that has green tea extract complexed with iron. This therapeutic approach leverages the beneficial properties of green tea extract in combination with iron to ameliorate the symptoms of ulcerative colitis.

In implementations, the specific dosage provided to the patient is considered to be a therapeutically effective amount, which is determined based on factors such as the severity of the condition, patient weight, age, and general health.

Advantages for individuals seeking to improve their gastrointestinal health may include one or more of the following. The method improves the management of ulcerative colitis symptoms, and the beneficial effect is due to blocking vitamin k uptake or use by colonic bacteria. Therefore reducing or eliminating vitamin K by dietary choices and by not taking vitamin K by mouth (such as in many multivitamins) is also beneficial and enhances the effect. The plant extracts complexed with iron has demonstrated that the combination has beneficial properties due to modification of the microbial flora of the intestine in a manner that is beneficial for multiple gastrointestinal conditions including ulcerative colitis, Crohn's disease, irritable bowel syndrome, excessive gas, and bloating. Because of the systemic effects of the composition and metabolites of the intestinal microflora these compounds have widespread beneficial effects on multiple medical conditions and organ functions. By leveraging the therapeutic properties of natural plant sources, the one embodiment offers a more holistic approach to treating gastrointestinal conditions with a lower risk of side effects compared to synthetic pharmaceuticals. The encapsulation in delayed-release capsules allows the active ingredients to bypass the stomach and release in the lower gastrointestinal tract where they exert their maximum effect without being degraded by stomach acid. The color change that occurs upon forming the botanical-iron complex acts as a built-in indicator of successful chelation/complexation, facilitating quality control during manufacturing.

The development of a specific temperature and agitation protocol enables the maximization of the extraction yield and preserves the integrity of the active compounds, leading to a potent therapeutic extract. The powder or granular form of the final product is convenient for various dosage forms, including capsules, tablets, or sachets, providing ease of use and compliance. Preliminary studies and user reports indicating the effectiveness of the botanical-iron complex support the validity of the formulation, encouraging further research and potential widespread adoption.

The method of production utilizes simple and relatively low-cost extraction and drying techniques suited for large-scale manufacturing without the need for expensive solvents or equipment. Using plant-based resources and water as the primary extraction solvent aligns with green chemistry principles, minimizing environmental impact. The foregoing advantages highlight the unique contribution of the one embodiment to the field of gastrointestinal therapeutics and underscore its potential to offer patients a safe, effective, and natural alternative for managing their conditions. Other benefits may include one or more of the following:

Extended Benefits: The green tea extracts chelated/complexed with iron may not only target the gastrointestinal tract but may also offer systemic benefits, thereby addressing extraintestinal conditions that might be related to intestinal bacterial metabolism which can cause inflammation and oxidative stress.

Broad Therapeutic Applications: The one implementation may provide a new approach in the treatment of various gastrointestinal disorders, including but not limited to ulcerative colitis, and irritable bowel syndrome, offering potential therapeutic benefits that extend beyond current conventional treatments.

Convenience and Versatility: The one implementation's final product form, as a fine granular or powder, allows for convenient incorporation into capsules, tablets, or functional foods and beverages, making it a versatile option for varying consumer preferences and lifestyles.

Natural and Safe: Utilizing natural compounds such as green tea extract and iron, the one implementation may be considered a safer alternative to pharmaceuticals, with a lower likelihood of adverse side effects, promoting better acceptance among individuals looking for natural health solutions.

Overall, one implementation has the potential to provide an innovative and holistic approach to gastrointestinal health through a chelation of green tea polyphenols and iron, yielding a composition that has enhanced therapeutic benefits, greatly surpassing the benefits of either component alone, while minimizing the drawbacks traditionally associated with other available therapies.

DETAILED DESCRIPTION OF THE INVENTION

Figure 1:
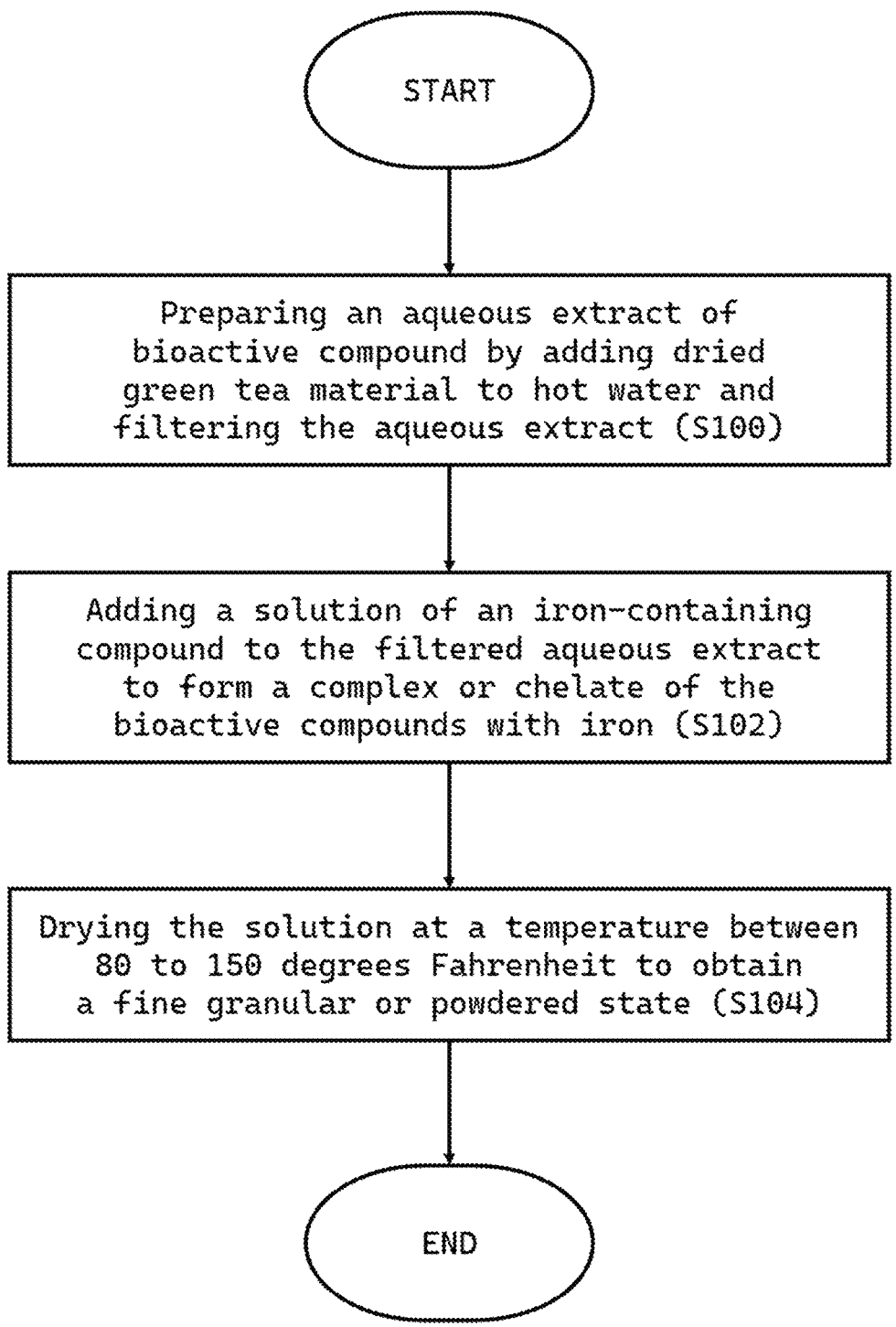
FIG. 1 shows an exemplary flowchart describing the preparation of an iron-complexed green tea extract.

FIG. 1 is a flowchart illustrating the steps involved in preparing an iron-complexed green tea extract. As an overview, the process starts with preparing an aqueous extract of bioactive compounds by adding dried green tea material to hot water and filtering the extract (S100). Following this, a solution of an iron-containing compound is added to the filtered extract to form a complex or chelate of the bioactive compounds with iron (S102). Finally, the solution is dried at a temperature between 80 to 150 degrees Fahrenheit to obtain a fine granular or powdered state (S104).

Reviewing FIG. 1 in detail, the method involves preparing an aqueous extract of bioactive compounds, which is initiated by adding dried green tea material to hot water. The temperature of the hot water ranges from 100 to 200 degrees Fahrenheit and is subjected to mild agitation for approximately 3 minutes. Following this, the aqueous extract is filtered to remove any solid residues, resulting in a purified extract ready for further processing. This step is essential to ensure that the bioactive compounds are efficiently extracted and purified, laying the foundation for subsequent processing steps detailed under S100.

The method comprises preparing an aqueous extract of bioactive compounds by adding dried green tea material to hot water, followed by filtering the aqueous extract (S100). Following this, a solution of an iron-containing compound, selected from ferrous sulfate, ferrous gluconate, ferric chloride, ferrous fumarate, or other iron containing compounds capable of dissociation in aqueous solution to provide iron ions, is introduced to the filtered aqueous extract (S102). This incorporation initiates the formation of a complex or chelate between the bioactive compounds and the iron. Once the complex formation is complete, the solution containing the bioactive iron complex is subjected to a drying process. The solution is dried at a temperature maintained between 80 to 150 degrees Fahrenheit. This drying can be achieved through methods such as spray drying or dehydrating at low heat to ensure that the bioactive compounds remain in a fine granular or powdered state without degradation of their biological activity. In one example, the resulting solution is dried at temperatures ranging from 80 to 150 degrees Fahrenheit to obtain the final product in a fine granular or powdered state (S104). This product is then suitable for consumption or further processing. The chelate/complex of iron and green tea extract (and other sources of polyphenols such as eggplant) is therapeutic in a number of gastrointestinal and extraintestinal conditions. Polyphenols (such as green tea extract) alone do not have these properties, and neither does iron alone. As detailed below, the chelation/complex of iron and polymphenols has beneficial effects many orders of magnitude greater than the components alone.

Figure 2:
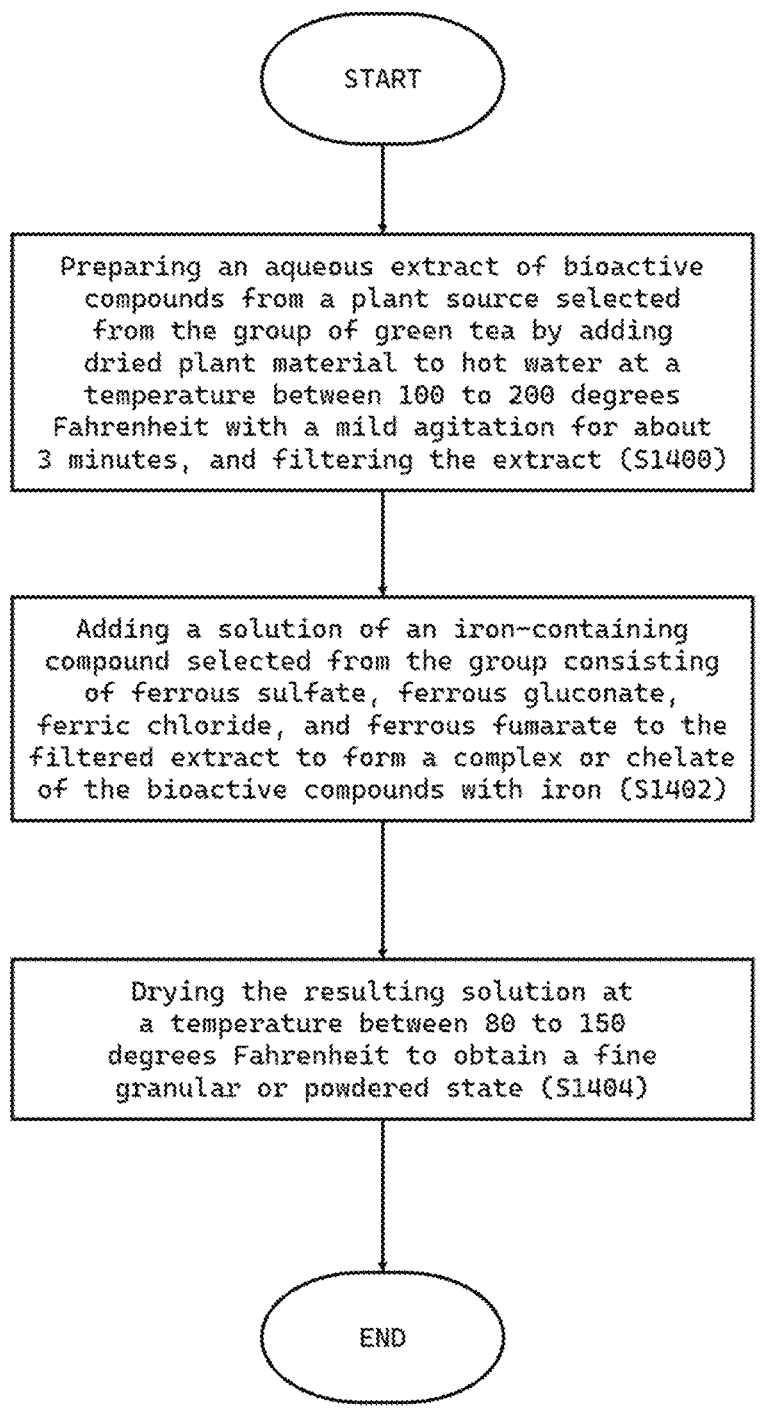
FIG. 2 shows another exemplary flowchart for making an iron-complexed green tea extract.

Referring now to FIG. 2, another process for making an iron-complexed green tea extract is shown. Initially, an aqueous extract rich in bioactive compounds is prepared by adding dried green tea material to hot water at a temperature between 100 to 200 degrees Fahrenheit with mild agitation for approximately 3 minutes and subsequently filtering the extract (S1400). Thereafter, a solution of an iron-containing compound selected from the group consisting of ferrous sulfate, ferrous gluconate, ferric chloride, and ferrous fumarate is added to the filtered extract to form a complex or chelate of the bioactive compounds with iron (S1402). The resultant solution is then dried at a temperature ranging from 80 to 150 degrees Fahrenheit to obtain a product in a fine granular or powdered state (S1404). The product thus obtained is suitable for consumption or further processing and is intended to facilitate the management of ulcerative colitis symptoms, leveraging the beneficial properties of the green tea extract when combined with iron.

Chelation with iron induces structural changes in the plant extracts, which can be identified through chromatography. Suitable iron-containing compounds include but are not limited to ferrous sulfate, ferrous gluconate, ferric chloride, ferrous fumarate, or other ferric or ferrous iron compounds capable of forming complexes or chelates with the bioactive compounds present in the green tea extract. The formation of a complex or chelate is indicated by a noticeable color change in the solution, signifying a structural modification in the bioactive compounds. These structural modifications result in a unique composition that enhances the biological activity and health benefits of the compounds, improving their effectiveness in treating gastrointestinal and other related conditions.

In one implementation, the method includes drying the resulting solution at a temperature between 80 to 150 degrees Fahrenheit to obtain a fine granular or powdered state (S1404). This drying step follows the introduction of an iron-containing compound to the filtered extract which forms a complex or chelate with the bioactive compounds. The controlled drying temperature ensures the preservation of the bioactive properties while achieving the desired physical form of the product. The fine granular or powdered state produced in this manner is suitable for direct consumption or further processing, facilitating its use in promoting gastrointestinal health and addressing related conditions.

The formulation can modify the microbial flora of the intestine, providing benefits for gastrointestinal conditions including ulcerative colitis, Crohn's disease, irritable bowel syndrome, excessive gas, and bloating. The systemic effects of these compositions on the metabolism of intestinal microflora result in widespread improvements across multiple medical conditions and organ functions. Additionally, it can address other health conditions associated with the metabolic products of intestinal flora, including arthritis, fatigue, and cognitive symptoms such as "brain fog." The iron-complexed green tea extract thus offers a unique and potent approach to improving gastrointestinal and overall health. The beneficial effect of the compound would be obtained by taking one capsule by mouth with each meal (three times per day).

The resultant dried solution possesses unique properties that significantly inhibit the metabolism of colonic bacteria, which relates to the modulation of the intestinal microflora composition and activity. By altering the metabolic activities of colonic bacteria, these compounds can reduce the production of harmful metabolites often associated with gastrointestinal conditions such as ulcerative colitis, Crohn's disease, irritable bowel syndrome, and excessive gastrointestinal gas. This inhibition mechanism also reduces inflammation, gas, diarrhea, bleeding, and abdominal symptoms such as bloating, pain, and cramping.

Additionally, this alteration of the colonic bacterial metabolism has systemic effects beyond the gastrointestinal tract, providing therapeutic benefits for extratestinal conditions associated with alterations in the composition and metabolism of the intestinal microflora. For example, joint pain from Arthritis, fatigue, and mental status changes such as "brain fog" have shown improvement. The bioactive compounds in the dried solution may include polyphenols and other high-bioactivity chemicals complexed with iron, enhancing their biological activity when introduced into the colonic environment. This enhancement in biological effectiveness can also be achieved with synthetically produced analogues of these compounds, ensuring consistency in therapeutic outcomes.

One example includes administering alpha-tocopherylquinone in combination with the dried green tea extract plus iron. The combination further enhances the therapeutic activity of the green tea extract chelated/complexed with iron. The further addition of eggplant extract plus iron can also increase the therapeutic effect as can the combination of all three compounds (green tea extract chelated/complexed with iron, eggplant extract complexed/chelated with iron and alpha-tocopherylquinone in one formulation which can act synergistically on the intestinal flora to produce beneficial therapeutic effects. This combined administration is particularly advantageous for treating conditions such as ulcerative colitis, Crohn's disease, and irritable bowel syndrome. The co-administration of alpha-tocopherylquinone with the modified plant extract amplifies the therapeutic effects, improving mucosal healing and reducing symptoms like bloating, pain, and gastrointestinal discomfort. This combination therapy is designed to take advantage of the synergistic effects of these compounds, providing a more comprehensive treatment approach to inflammatory and functional gastrointestinal disorders. By integrating the known benefits of alpha-tocopherylquinone with the modified plant extracts complexed with iron, the one implementation presents an advanced method for enhancing intestinal health and treating related disorders. The process of creating the iron-complexed plant extract and the method of combining it with alpha-tocopherol are specifically tailored to ensure optimal therapeutic efficacy. The encapsulated form allows for targeted delivery to the lower gastrointestinal tract, where the active compounds are most needed. This strategic approach ensures that the beneficial properties of both the plant extract and alpha tocopherylquinone are maximally utilized, offering a more effective treatment option compared to existing therapies. The described method can be adapted to include other plant extracts and bioactive compounds, broadening the scope and potential applications of the one implementation in enhancing human health.

Another example includes administering the dried solution with a diet low in vitamin K. Other applications of the one implementation would be in enhancing animal health such as veterinary medicine and animal husbandry such as enhancing the health, growth rate, or productivity of raising animals for meat, eggs, dairy products and enhancing plant growth and/or productivity by altering the composition and/or metabolism of the microflora of the growth medium of the plants and providing beneficial effects.

The compound can be used in treating extra-intestinal medical conditions associated with metabolic products of intestinal flora alterations, such as arthritis, arthropathies, fatigue, and mental status changes commonly referred to as "brain fog."

Examples of Beneficial Effects of Green Tea Extract Chelated/Complexed with Iron (GTE+Fe)

The following series of experiments and observations show how the chelate/complex of polyphenols provides markedly improved therapeutic effects over either component alone in altering the intestinal microbial flora and treating gastrointestinal and extraintestinal conditions such as ulcerative colitis, Crohn's disease, irritable bowel syndrome, inflammation, gas, bloating and exdtraintestinal symptoms associated with an altered intestinal flora such as athropathies and arthritis, wound healing and mental fog.

These effects were observed in a patient with continuously active ulcerative colitis (UC). Many patients with ulcerative colitis have remitting/recurring disease activity which occurs spontaneously at random times. Other factors, such as changes in diet, stress, intercurrent use of medications either to control symptoms of UC or used to treat other conditions, such as antibiotics non steroidal pain medications and steroids, may make inflammation and symptoms worse or better depending on their particular properties.

Some patients with UC have unremitting continuously active disease which never goes into remission spontaneously. Such patients make excellent study subjects since the action of compounds designed to reduce disease activity and symptoms can be evaluated without the complicating factor of spontaneous changes in disease severity.

In the patient studied in this report disease activity was observed over several decades and was continuously active with no spontaneous remissions. The following observations were made:

1. When disease activity had been well controlled for months with no significant symptoms by the daily use of green tea extract chelated/complexed with iron (GTE+Fe), when GTE+Fe was stopped to see if sustained remission had been attained, the symptoms (cramping, diarrhea, blood in stool arthropathies, skin lesions) returned within three days and remained present until GTE+Fe was resumed. Alleviation of disease symptoms occurred within one week of resumption of GTE+Fe. This was repeated more than 5 times over several years and the same results were consistently observed.

2. On multiple occasions over the same time period GTE+Fe was stopped due to unforeseen circumstances, such as prolonged trips when capsules were used up or unavailable, and disease activity again increased, the symptoms were brought under control by reintroduction of GTE+Fe.

3. When experiments were undertaken to determine the most effective form of encapsulation to enhance the beneficial effects of GTE+Fe, and what turned out to be less effective dosage forms were tested, the disease activity became more pronounced and remission was again obtained by going back to the most effective encapsulation form. (Since GTE+Fe is degraded under acid conditions, encapsulation with enteric coated and delayed release capsules are much more effective than plain capsules of various compositions since they protect the GTE+Fe from degradation in gastic acid).

4. Additional beneficial effects of GTE+Fe noted during the time period described above was more rapid healing of wounds. During exacerbations of disease activity induced as described above, lesions of pyoderma gangrenosum were apparent on the lower extremities of the patient. These lesions, which are notoriously difficult to heal, healed more quickly and completely than previously in this patient and more quickly than seen in any other observed patients over decades of gastroenterology practice.

5. Cuts and punctures sustained through minor traumas also healed more rapidly than previously observed 6. Arthritis pain and stiffness in hands, fingers, hips and lower back was greatly reduced by GTE+Fe.

7. Flatulence (the volume and frequency of passed gas) was greatly decreased by GTE+Fe as well as the odor of passed gas being reduced (despite a vegetarian diet high in legumes)

8. Bloating and abdominal pain and alteration of bowel habits (the hallmarks of IBS) were greatly reduced by GTE+Fe In another patient with altered bowel habits abdominal pain gas and bloating (the hallmarks of IBS) but no evidence of inflammatory bowel disease these symptoms were greatly reduced by GTE+Fe.

While green tea is preferred, other plant extracts high in bioactive compounds could potentially provide similar benefits when chelated/complexed with iron. Suitable extracts can be identified by a color change from lighter colors to a deep black color when reacted with iron. In experiments with many different plant extracts the beneficial therapeutic effects were found to be directly related to the intensity of the color change.

Further, while the capsule form is preferred and is effective in reducing gastrointestinal inflammation in the small intestine and colon, such as inflammation caused by Crohn's disease and ulcerative colitis, other delivery mechanisms can be used. For example, as a suppository, the compound can be used with fats, waxes, excipients, and binders, as is the usual practice in making suppositories. The suppository may contain about 1 to about 20 mg of extract per 50 mg of suppository. It is administered rectally and will dissolve at body temperature and deliver the active component to the colon. The suppository may be used to treat hemorrhoids, colitis, proctitis, and other conditions. A rectal foam may be prepared by combining the extract with a foaming agent, such as cetyl alcohol, propylene glycol or lecithin. The amount of extract in the foam may be about 20 to about 500 mg per 10 mg of foaming agent. The foam may be administered into the rectum for the treatment of inflammation of the rectum and hemorrhoids. The extract may be diluted with water and used directly as an enema or it may be freeze dried or sprayed dried then reconstituted with water for use as an enema. An amount of extract of about 15 to about 150 mg per 200 ml may be used as an enema for treating colitis and proctitis of the large intestine, such as Crohn's disease and ulcerative colitis. Other suitable delivery mechanisms are also contemplated.

As various modifications could be made in the constructions and methods herein described and illustrated without departing from the scope of the disclosure, it is intended that all matter contained in the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entirety.

The invention claimed is:

1. A method for treating a gastrointestinal condition, comprising:
   preparing an aqueous extract of bioactive compound by adding dried green tea material to water and filtering the aqueous extract;
   adding a solution of an iron-containing compound to the filtered aqueous extract to form a complex or chelate of the bioactive compounds with iron at a neutral pH;
   drying the solution at a temperature between 80 to 150 degrees Fahrenheit to obtain a granular or powdered state; and
   providing the solution in a package for a user to ingest to treat the gastrointestinal condition.

2. The method of claim 1, wherein the iron-containing compound is selected from one of ferrous sulfate, ferrous gluconate, ferric chloride, ferrous fumarate, and an iron containing compound providing free iron in a solution.

3. The method of claim 1, comprising encapsulating the dried complex or chelate into a delayed-release capsule or pill.

4. The method of claim 1, wherein the complex or chelate of the bioactive compounds with iron is formed with a color change.

5. The method of claim 1, wherein the dried solution is administered three times per day with meals.

6. The method of claim 1, wherein the dried solution reduces inflammation in the colon, bloating and gas.

7. The method of claim 1, further comprising administering alpha-tocopherylquinone or eggplant extract plus iron or both in combination with the dried solution.

8. The method of claim 1, comprising administering the dried solution with a diet low in vitamin K.

9. The method of claim 1, comprising administering the solution to a subject to alter the intestinal flora to reduce inflammation, gas, diarrhea, bleeding, or abdominal symptoms.

10. A method for treating a gastrointestinal condition, comprising:
    preparing an aqueous extract of bioactive compounds from a plant source selected from the group consisting of green tea by adding dried plant material to water at a temperature between 100 to 200 degrees Fahrenheit with a mild agitation for about 3 minutes, and filtering the extract;
    adding a solution of an iron-containing compound selected from one of ferrous sulfate, ferrous gluconate, ferric chloride, ferrous fumarate, and an iron ion containing compound providing free iron in a solution to the filtered extract to form a complex or chelate of the bioactive compounds with iron at a neutral pH;
    drying the resulting solution at a temperature between 80 to 150 degrees Fahrenheit to obtain a granular or powdered state; and
    providing the solution in a package for a user to ingest to treat the gastrointestinal condition.

11. A method of claim 1 for treating ulcerative colitis in a patient, comprising administering a therapeutically effective amount of a composition comprising a green tea extract complexed with iron.

12. The method of claim 11, wherein the composition is administered orally in a delayed-release capsule.

13. The method of claim 11, comprising:
    preparing an aqueous extract of bioactive compound by adding dried green tea material to hot water and filtering the aqueous extract;

adding a solution of an iron-containing compound to the filtered aqueous extract to form a complex or chelate of the bioactive compounds with iron;

drying the solution at a temperature between 80 to 150 degrees Fahrenheit to obtain a granular or powdered state.

\* \* \* \* \*